(12) United States Patent
Leona

(10) Patent No.: US 7,362,431 B2
(45) Date of Patent: Apr. 22, 2008

(54) NON-INVASIVE IDENTIFICATION OF FLUORESCENT DYES IN HISTORIC TEXTILES BY MATRIX TRANSFER-SURFACE ENHANCED RAMAN SCATTERING

(75) Inventor: Marco Leona, New York, NY (US)

(73) Assignee: The Metropolitan Museum of Art, New York, NY (US)

( * ) Notice: Subject to any disclaimer, the term of this patent is extended or adjusted under 35 U.S.C. 154(b) by 128 days.

(21) Appl. No.: 11/463,361

(22) Filed: Aug. 9, 2006

(65) Prior Publication Data
US 2007/0035729 A1 Feb. 15, 2007

Related U.S. Application Data

(60) Provisional application No. 60/707,468, filed on Aug. 11, 2005.

(51) Int. Cl.
G01J 3/44 (2006.01)
G01N 21/65 (2006.01)
(52) U.S. Cl. .................................. 356/301; 356/36
(58) Field of Classification Search .............. 356/36, 356/301
See application file for complete search history.

(56) References Cited

U.S. PATENT DOCUMENTS 6,623,977 B1 9/2003 Farquharson et al.
6,649,683 B2 11/2003 Bell
6,943,031 B2 9/2005 Farquharson et al.
6,943,032 B2 9/2005 Farquharson et al.
7,022,288 B1 4/2006 Boss

OTHER PUBLICATIONS

Schweppe, H, and Winter, J., "Madder and Alizarin" in West Fitzhugh, E. (editor) Artists' pigments; a handbook of their history and characteristics, vol. 3, National Gallery of Art, Washington (1997) 109-135.
Schweppe, H., and Roosen-Runge, H., "Carmine—cochineal carmine and kermes carmine" in Feller, R.L. (editor) Artists' pigments, A handbook of their history and characteristics, vol. 1, National Gallery of Art, Washington (1986) 255-283.
Wouters, J. "High performance liquid chromatography of anthraquinones: analysis of plant and insect extracts and dyed textiles," Studies in Conservation (1985) 30(3) 119-127.
Leona, M. IRUG Proceedings Volume of the Sixth Infrared and Raman Users Group Conference, Florence (I) 29.03-01.04.2004, Editor Marcello Picollo, Publisher II Prato (Padova, Italy) 2005, 105-112.

(Continued)

*Primary Examiner*—F. L Evans
(74) *Attorney, Agent, or Firm*—Mark Montague; Cowan, Liebowitz & Latman, P.C.

(57) ABSTRACT

A new process is presented to non-invasively identify organic dyes in historic textiles and other works of art. A small gel bead loaded with a SERS substrate is used to gently extract microscopic amounts of dyes from works of art, without the need to remove a sample and separately extract the dye by acid hydrolysis of the fiber-mordant-dye system. The gel bead subsequently is coated with a silver, gold or copper colloid or with silver, gold or copper nanoislands, and is examined in accordance with a surface enhanced Raman scattering technique to identify the dye.

19 Claims, 4 Drawing Sheets

OTHER PUBLICATIONS

Canamares MV, Garcia-Ramos JV, Domingo C, Sanchez-Cortes S. J. Raman Spectrosc, Surface-enhanced Raman Scattering Study of the Absorption of the Anthraquinone Pigment Alizarin on Ag nanoparticles; 2004; Journal of the Raman Spectroscopy 35: 921-927.

Shadi IT, Chowdry BZ, Snowden MJ, Whitnall R. J. Raman Spectrosc; Semi-quantitative analysis of alizarin and purpurin by surface-enhanced resonance Raman spectroscopy (SEERS) using Silver Colloids; 2004; Journal of the Raman Spectroscopy 35: 800-807, Leona M., Proceedings of SPIE vol. 5993, 59930L-1, 2005.

Fleischmann, M., Hendra, P.J., and McQuillan, A.J., "Raman spectra of pyridine adsorbed at a silver electrode," Chemical Physic Letters (1974) 26(2) 163-166.

Jeanmaire, D.L., and Van Duyne, R.P., "Surface Raman spectroelectrochemistry. Part 1: heterocyclic, aromatic, and aliphatic amines adsorbed on the anodized silver electrode," Journal of Electroanalytical Chemistry (1977) 84(1) 1-20.

Nie, S., and Emory, S.E., "Probing single molecules and single nanoparticles by surface-enhanced Raman scattering," Science (1997) 275 1102-1106.

Kneipp, K., Wang, Y., Kneipp, H., Perelman, L.T., Itzkan, I., Dasari, R.R., and Feld, M.S., "Single molecule detection using surface-enhanced Raman scattering (SERS)," Physical Review Letters (1997) 78(9) 1667-1670.

Campion, A. and Kambhampati, P., "Surface-enhanced Raman scattering," Chemical Society Reviews (1998) 27 241-250.

Shoute, L.C., and Loppnow, G.R., "Excited state dynamics of alizarin-sensitized TiO2 nanoparticles from resonance Raman spectroscopy," Journal of Chemical Physics (2002) 117(2) 842-850.

Lee, P.C., and Meisel, D., "Adsorption and surface-enhanced Raman of dyes on silver and gold sols," Journal of Physical Chemistry (1982) 86 3391-3395.

Tiedemann, E.J., and Yang, Y., "Fiber safe extraction of red mordant dyes from hair fibers," Journal of the American Institute for Conservation (1995) 34(3) 195-206; Bell, S.E.J.

Bell, Steven E.J.; Spence Stephen J.; Disposable, stable media for reproducible surface-enhanced Raman Spectroscopy; The Royal Society of Chemistry 2001; pp. 1-3.

Farquharson, Stuart and Maksymiuk Paul; Simultaneous Chemical Separation and Surface-Enhanced Raman Spectral Detection Using Silver-Doped Sol-Gels; Applied spectroscopy, vol. 57, No. 4, 2003, pp. 479-481.

Albrecht, M.G., and Creighton, J.A. Anomalously intense Raman spectra of pyridine at a silver electrode; Journal of the American Chemical Society (1997) 99 5215-5227.

Farquharson, S., and Maksymiuk, P., "Simultaneous chemical separation and surface enhanced Raman spectral detection using silver doped sol-gels," Applied Spectroscopy (2003) 57(4) 479-481.

Spence, S.J., and Bell, E.J., "Disposable, stable media for reproducible surface-enhanced Raman spectroscopy," Analyst (2001) 126 (1), 1-3.

Natural anthraquinone dyes: alizarin; purpurin; carminic acid; laccaic acids

SERS spectrum of alizarin in Ag colloid with poly-L-lysine
(the lower line is the spectrum of an Ag and NaOH blank):
poly-L-lysine is used to facilitate adsorption of the dye on the Ag nanoparticles.

MT-SERS spectra from a madder dyed textile from the reference collection at the Metropolitan Museum of Art, and from a 10th Century archaeological sample.

NON-INVASIVE IDENTIFICATION OF FLUORESCENT DYES IN HISTORIC TEXTILES BY MATRIX TRANSFER-SURFACE ENHANCED RAMAN SCATTERING

REFERENCE TO RELATED APPLICATION

This application claims the benefit of U.S. Provisional Patent Application Ser. No. 60/707,468, filed Aug. 11, 2005, the disclosure of which is incorporated herein by reference.

FIELD OF THE INVENTION

This invention relates to identifying organic dyes in works of art.

BACKGROUND OF THE INVENTION

The identification of dyes and organic colorants in works of art is one of the most difficult problems in the field of scientific studies of cultural heritage.

Organic colorants are, by definition and by economic necessity, molecules with high extinction coefficients in the visible radiation range. In other words, organic colorants provide intense coloration even when used in small quantities. The actual amount of organic dye present in a dye fiber or contained as an insoluble lake in a paint sample is extremely small. Only the most sensitive microanalytical, or better, non-invasive techniques can be used to identify an organic dye in works of art.

Various natural anthraquinone dyes, including alizarin, purpurin, carminic acid, and laccaic acids, such as shown in FIG. 1, are examples of important natural products that are extremely difficult if not impossible to analyze by dispersive Raman spectroscopy. Anthraquinones are mordant dyes: they are used not in their free form, but as insoluble complexes with aluminum or other metal ions. These dies are discussed in the following publications: Schweppe, H, and Winter, J., "Madder and Alizarin" in West Fitzhugh, E. (editor) Artists' pigments; a handbook of their history and characteristics, Volume 3, National Gallery of Art, Washington (1997) 109-142; and Schweppe, H., and Roosen-Runge, H., "Carmine—cochineal carmine and kermes carmine" in Feller, R. L. (editor) Artists' pigments, A handbook of their history and characteristics, Volume 1, National Gallery of Art, Washington (1986) 255-283, the disclosures of which are incorporated herein by reference. The same dyes are also found as pigments in works of art such as drawings, illuminated manuscripts, prints, and paintings, where they are found as "lake pigments", that is, insoluble complexes of the dye molecule with a poly-valent metal cation. Used as writing inks, the lakes derived from these dyes and from synthetic organic dyes could also be found in written or printed documents.

Organic dyes in historic textiles currently are identified by High Performance Liquid Chromatography, which is discussed in Wouters, J. "High performance liquid chromatography of anthraquinones: analysis of plant and insect extracts and dyed textiles," Studies in Conservation (1985) 30(3) 119-128, the disclosure of which is incorporated herein by reference. In practice, this process involves removing a sample of up to 5 mm of threads of the textile and carrying out hydrolysis/extraction separation with an acidic solution. Due to the required sample size, this process is ill-suited to identify the organic dyes in paintings and other works of art where sufficient samples cannot be obtained.

Natural dyes in works of art have been identified by the use of surface enhanced Raman scattering (hereinafter "SERS") methods. Various publications that discuss surface enhanced Raman scattering include: Leona, M. IRUG Proceedings Volume of the Sixth Infrared and Raman Users Group Conference, Florence (I) 29.03-01.04.2004, Editor Marcello Picollo, Publisher II Prato (Padova, Italy) 2005, 105-112; Canamares M V, Garcia-Ramos J V, Domingo C, Sanchez-Cortes S. J. Raman Spectrosc. 2004; 35: 921-927; Shadi I T, Chowdry B Z, Snowden M J, Whitnall R. J. Raman Spectrosc. 2004; 35: 800-807, Leona M., Proceedings of SPIE Vol. 5993, 59930L-1, 2005, the disclosures of which are incorporated herein by reference.

SERS is a complex effect observed when organic molecules are adsorbed on atomically rough metal surfaces. See, for example, Fleischmann, M., Hendra, P. J., and McQuillan, A. J., "Raman spectra of pyridine adsorbed at a silver electrode," Chemical Physic Letters (1974) 26(2) 163-166; Jeanmaire, D. L., and Van Duyne, R. P., "Surface Raman spectroelectrochemistry. Part 1: heterocyclic, aromatic, and aliphatic amines adsorbed on the anodized silver electrode," Journal of Electroanalytical Chemistry (1977) 84(1) 1-20; Albrecht, M. G., and Creighton, J. A., "Anomalously intense Raman spectra of pyridine at a silver electrode," Journal of the American Chemical Society (1977) 99 5215-5227; Nie, S., and Emory, S. E., "Probing single molecules and single nanoparticles by surface-enhanced Raman scattering," Science (1997) 275 1102-1106; Kneipp, K., Wang, Y., Kneipp, H., Perelman, L. T., Itzkan, I., Dasari, R. R., and Feld, M. S., "Single molecule detection using surface-enhanced Raman scattering (SERS)," Physical Review Letters (1997) 78(9) 1667-1670; and Campion, A. and Kambhampati, P., "Surface-enhanced Raman scattering," Chemical Society Reviews (1998) 27 241-250, the disclosures of which are incorporated herein by reference.

In short, when studying by Raman spectroscopy organic molecules adsorbed on atomically rough metal surfaces, the incident (laser) and scattered (Raman) electromagnetic fields are intensified by resonance with the metal plasmon (the surface electrons standing wave). Additionally, interactions between the energy levels of the metal and of the molecule can lead to resonance conditions or quench any fluorescence through ultrafast electron transfer from the molecule excited states to the metal, as discussed in Shoute, L. C., and Loppnow, G. R., "Excited state dynamics of alizarin-sensitized TiO2 nanoparticles from resonance Raman spectroscopy," Journal of Chemical Physics (2002) 117(2) 842-850, the disclosure of which is incorporated herein by reference.

The observation of single molecule Raman spectra from species that are known to be fluorescent implies that SERS produces an enhancement of the Raman effect of up to 14 orders of magnitude. This enhancement has tremendous implications towards ultra-sensitive detection of natural dyes in works of art, the technique is extremely promising for analyzing microscopic samples of lake pigments and dyed fibers. While SERS is in theory possible with any nanosized metal support, in practice, plasmon resonance limits the metals which support SERS to those which show plasmon resonance at the wavelength commonly used for Raman excitation: these are most commonly gold, silver and copper. In the course of this study, silver was elected as the most effective support. The nanoscale roughness condition was satisfied by using solution-reduced colloids, a very common SERS support, prepared following the procedure described in Lee, P. C., and Meisel, D., "Adsorption and surface-enhanced Raman of dyes on silver and gold sols,"

Journal of Physical Chemistry (1982) 86 3391-3395, the disclosure of which is incorporated herein by reference.

SERS has been proven to allow detection of alizarin, the main constituent of the historical dye madder (from the root of *Rubia tinctorum* L.) at picogram levels (in Leona, IRUG Proceedings, referenced above) and of other dyes (Leona, Proceedings of SPIE, referenced above). Current procedures for SERS of works of art however still require that a sample be removed from the work of art to hydrolyze the dye-mordant-fiber complex and bring the dye into solution. The dye solution is then mixed with the silver colloid and its Raman spectrum measured. FIG. 2 shows the SERS spectrum of alizarin in a silver colloid with poly-L-lysine (the lower line is the spectrum of an Ag and NaOH blank): poly-L-lysine is used to facilitate adsorption of the dye on the silver nanoparticles.

Other publications pertinent to the field include Tiedemann, E. J., and Yang, Y., "Fiber safe extraction of red mordant dyes from hair fibers," Journal of the American Institute for Conservation (1995) 34(3) 195-206; Bell, S. E. J., and Spence, S. J., "Disposable, stable media for reproducible surface-enhanced Raman spectroscopy," Analyst (2001) 126 (1), 1-3; and Farquharson, S., and Maksymiuk, P., "Simultaneous chemical separation and surface enhanced Raman spectral detection using silver doped sol-gels," Applied Spectroscopy (2003) 57(4) 479-481, the disclosures of which are incorporated herein by reference.

Various patents related to the field include U.S. Pat. No. 7,022,288 entitled "Chemical Detection Sensor System"; U.S. Pat. No. 6,943,032 entitled "Chemical separation and plural point, surface enhanced Raman spectral detection using metal doped sol-gels"; U.S. Pat. No. 6,943,031 entitled "Simultaneous Chemical separation and surface enhanced Raman spectral detection using metal doped sol-gels"; U.S. Pat. No. 6,649,683 entitled "Solid matrices for surface enhanced Raman spectroscopy"; and U.S. Pat. No. 6,623,977 entitled "Materials for surface-enhanced Raman spectroscopy, and SER sensor and method for preparing same", the disclosures of which are incorporated herein by reference.

OBJECTS AND SUMMARY OF THE INVENTION

It is therefore an object of the present invention to provide a process for identifying natural and synthetic organic dyes used as mordant dyes, direct dyes, vat dyes, pigment dyes, or lake pigments, in historic textiles, other works of art, and written and printed documents without removing a sample from the work under examination.

It is a further object of the present invention to provide a process for identifying organic dyes in historic textiles and other works of art, and written and printed documents without a separate hydrolysis/extraction step.

In accordance with an embodiment of the present invention, a process is provided for identifying an organic dye in a work, comprising applying a bead of a polymer gel to a portion of a work, removing the bead from the work, applying a SERS substrate to the bead, and examining the bead in accordance with a surface enhanced Raman scattering technique.

As an aspect of the invention, the polymer gel is selected from the group consisting of 2-hydroxyethyl methacrylate, 2,3-dihydroxypropyl methacrylate, a 1:1 random copolymer of 2,3 dihydroxypropyl methacrylate with 2-hydroxyethyl methacrylate, and a cross-linked hydroxyalkyl methacrylate.

As a further aspect of the invention, the bead is loaded with a solution containing at least water and a chelating agent.

As a feature of this aspect, the chelating agent is selected from the group consisting of ethylene diamine tetraacetic acid and a sodium salt of ethylene diamine tetraacetic.

As another aspect of the invention, the bead is loaded with a solution containing at least an organic solvent and a chelating agent.

As a feature of this aspect, the organic solvent is selected from the group consisting of dimethyl formammide, dimethyl sulfoxide and pyridine.

As another feature of this aspect, the amount of the chelating agent is selected to be in a range extending substantially between 0.1% (weight/volume) to a percentage value at saturation.

As yet a further aspect of the invention, the bead is loaded with a solution containing water, an organic solvent and a chelating agent.

As a feature of this aspect, the ratio of the water to the organic solvent is selected to be an intermediate value between 1:10 water/organic solvent and 10:1 water/organic solvent.

As yet another aspect of the invention, the SERS substrate is a silver, gold or copper colloid.

As yet a further aspect of the invention, the SERS substrate is comprised of silver, gold or copper nanoislands.

As a feature of this aspect, the silver, gold or copper nanoislands are produced by evaporation under high vacuum.

As another aspect of the invention, the polymer gel is formed directly on an end of a sensing device.

As a feature of this aspect, the sensing device is an optical fiber.

As a further feature of this aspect, the sensing device is a glass plate pre-coated with silver, gold, or copper nanoislands.

As an additional aspect of the invention, the bead is applied to the work for a period of substantially between 10 minutes and eight hours.

As yet a further aspect of the invention, examination is carried out without removing a sample from the work.

As yet another aspect of the invention, the organic dye in the work is identified from examining the bead in accordance with a surface enhanced Raman scattering technique.

As a feature of this aspect, the identified organic dye is an insoluble dye.

Various other objects, advantages and features of the present invention will become readily apparent to those of ordinary skill in the art, and the novel features will be particularly pointed out in the appended claims.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF CERTAIN PREFERRED EMBODIMENTS

The present invention entails a novel process of identifying organic dyes without removing a sample from the work under examination and also without a separate hydrolysis/extraction step. In accordance with the present invention, as described further below, the novel process is a matrix transfer surface enhanced Raman scattering, hereinafter also referred to as "MT-SERS," for the non-invasive identification of organic dyes in works of art, such as textiles, paintings, documents, and other items of interest. For purposes herein, the terms "work" or "work of art" are intended to include any material containing an organic dye in which its identification is desired, and includes but is not limited to textiles, paintings, other works of art, and items, documents and other materials generally not representing art.

The process of the present invention is highly sensitive and completely safe for works of art. Tests conducted on modern textiles dyed with traditional methods and materials show that dye analysis by matrix transfer SERS does not alter the color of the fabric noticeably and that no chemical residues are left on the textiles. The applicability of the method to severely deteriorated ancient textiles was demonstrated by the identification of alizarin in a textile fragment from the excavation of the 10th Century Byzantine site of Amorium, Turkey. Results obtained on alizarin as a model compound are reported herein. The inventive process has been demonstrated on other natural dyes, such as lawsone, hematoxylin, berberine, and purpurine.

Figure 1:
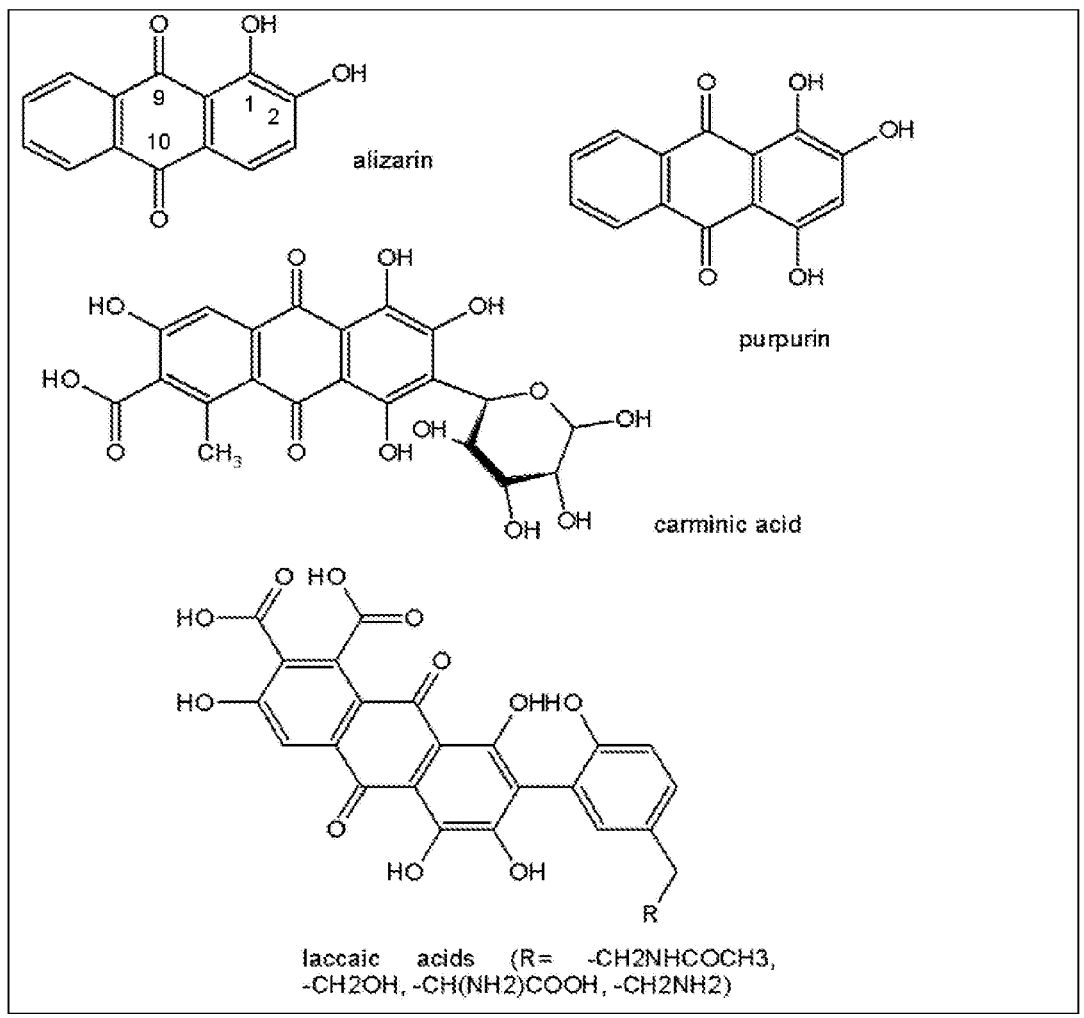
FIG. 1 shows natural anthraquinone dyes, including alizarin, purpurin, carminic acid, and laccaic acids.
Figure 2:
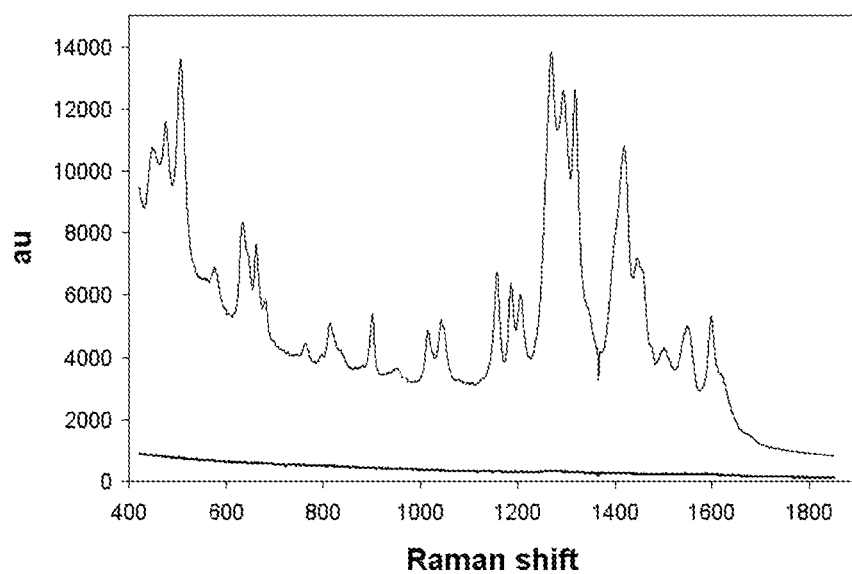
FIG. 2 shows the SERS spectrum of alizarin in a silver colloid with poly-L-lysine.
Figure 3:
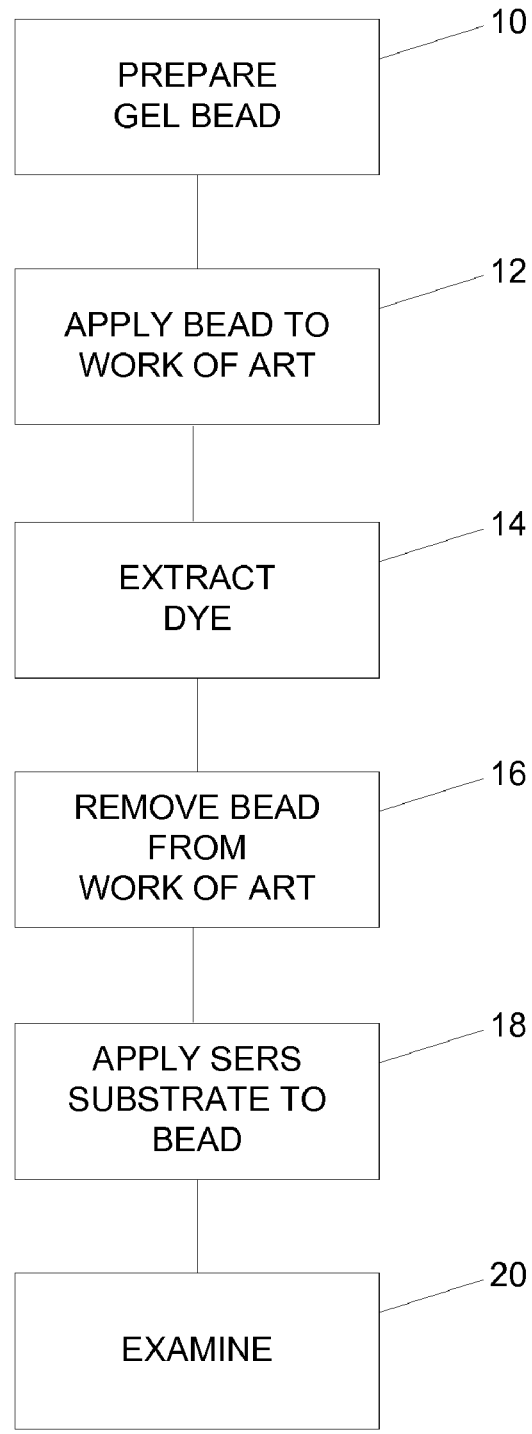
FIG. 3 shows a flow chart showing the general process of the present invention.

FIG. 3 illustrates a flow diagram showing the general, overall process of the present invention. Initially, a bead of a polymer hydrogel (or simply, "gel bead" or "bead") is prepared, as shown in step 10. The gel, prepared as further discussed below, is loaded with a solution containing water, an organic solvent, and a chelating agent. The bead then is applied to a work, in step 12. Upon applying the bead to the work, the dye-mordant-fabric system is broken down by the combined action of the chelating agent and the organic solvent, causing a microscopic amount of the uncomplexed dye to transfer to the gel, in step 14. Beneficially, using the gel as a medium for the solvent mixture confines its action only to the areas of the work covered by the gel bead. Extraction preferably is carried out for a period of between four (4) and eight (8) hours, and preferably at room temperature.

After sufficient time has passed for the extraction, the gel bead is removed from the work, in step 16, and transferred to a microscope slide or other appropriate surface. A SERS substrate is applied to the bead, in step 18. Finally, the bead is examined to identify the dye, in step 20, with a Raman microscope in any suitable manner known in the art.

Different hydrogels can be used for the MT procedure. In particular, the hydrogel may be 2-hydroxyethyl methacrylate (known as p(2-HEMA) or Benz 38 or HEMA); 2,3-dihydroxypropyl methacrylate; a 1:1 random copolymer of 2,3-dihydroxypropyl methacrylate with 2-hydroxyethyl methacrylate (Benz 5x, also known as GMA), or any cross-linked hydroxyalkyl methacrylate.

As an example, the gel may be prepared for use by soaking for 10 minutes to 1 hour in a solution of dimethyformammide (DMF) and water with EDTA or with EDTA-tetrasodium salt (Na-EDTA). Composition of the solution can range from DMF/Water 1:1 and EDTA or Na-EDTA 1% w/w, to DMF/Water 1:3 and saturated EDTA or Na-EDTA.

The chelating agent can be ethylene diamine tetraacetic acid or any of its sodium salts. Preferably, the amount of chelating agent varies between 0.1% (weight/volume) to its value at saturation.

The organic solvent can be dimethyl formammide, dimethyl sulfoxide, or pyridine. In alternative embodiments, the organic solvent is omitted, the water is omitted, or the ratio between the two takes intermediate values between 1:10 water/organic solvent and 10:1 water/organic solvent.

The SERS substrate applied to the gel subsequent to dye extraction may be a silver, gold or copper colloid. Absorption of organic dyes on the surface of the silver, gold or copper colloidal particles quenches the fluorescence that hinders observation of the ordinary Raman spectrum of alizarin, and gives rise to surface enhanced Raman scattering (SERS). If a silver colloid is used, it may be prepared in accordance with the procedure described in the publication Lee, P. C., and Meisel, D., "Adsorption and surface-enhanced Raman of dyes on silver and gold sols," identified above and incorporated herein by reference. Alternatively, instead of using a silver, gold or copper colloid to obtain the SERS effect, the gel fragment is coated with silver, gold or copper nanoislands produced by evaporation under high vacuum.

The hydrogel may be formed directly on the end of a sensing device such as an optical fiber or a glass plate previously coated with silver, gold, or copper nanoislands.

Figure 4:
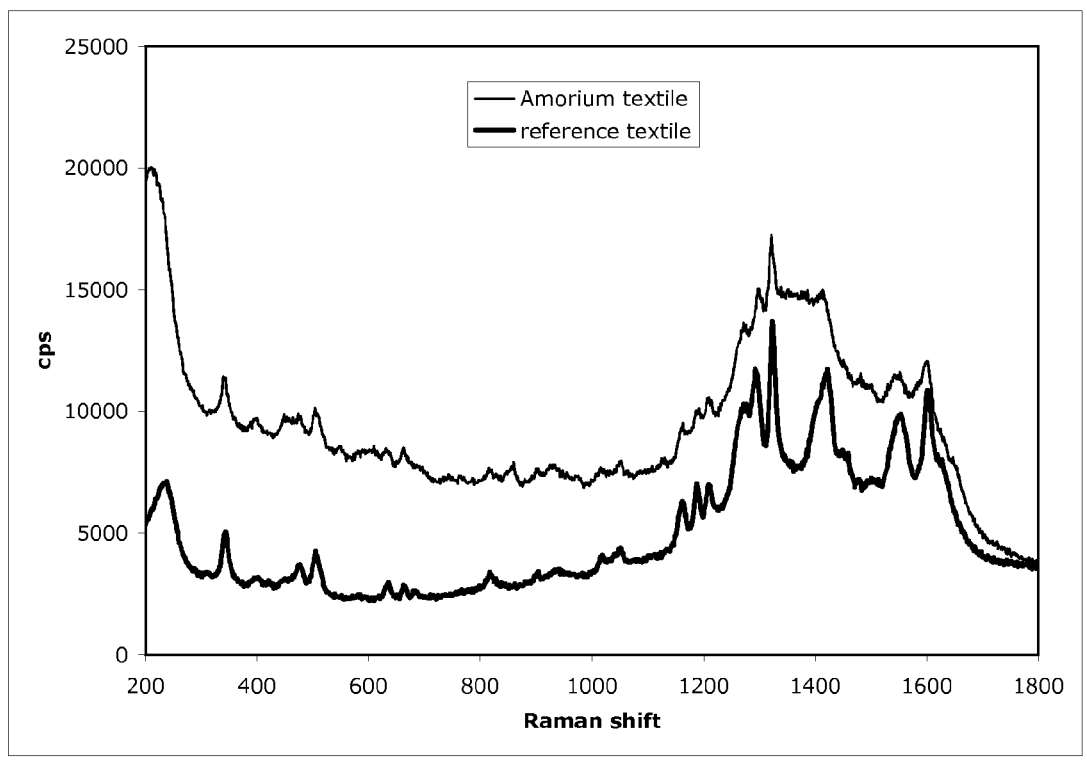
FIG. 4 shows the MT-SERS spectra in accordance with the present invention from a madder dyed textile from the reference collection at the Metropolitan Museum of Art, and from a 10th Century archaeological sample.

Data obtained from modern fabrics dyed with traditional method and materials, as well as from a 10th Century textile fragment show that MT-SERS is an efficient technique for the analysis of historic dyes, as shown in FIG. 4. FIG. 4 shows the MT-SERS spectra from a madder dyed textile from the reference collection at the Metropolitan Museum of Art, and from a 10th Century archaeological sample.

The procedures described herein provides for the transfer of a dye from a substrate to a gel without the need to remove a fragment from a work under examination. The amount of the dye removed from the work is negligible so that the human eye detects no appreciable fading. Moreover, in accordance with the present invention, the size of the polymer bead that may be utilized in the herein-described process can be of any size, and, if necessary or desired, may be a fraction of a millimeter (e.g., a diameter smaller than a millimeter, a diameter smaller than 0.1 mm) to minimize impact to works of art. The process of the present invention remains effective even with such tiny bead sizes. Still further, the one-step procedure combining extraction and hydrolysis is extremely efficient and time saving. Additionally, problems previously encountered in obtaining SERS spectra from alizarin (see, for example, Leona and Shadi IT references, referenced above) and due to its difficult adsorption on nanoparticles do not appear to affect its analysis by MT-SERS.

The procedure described herein is the first example of the use of a solvent gel to hydrolyze/extract insoluble dyes from a work for the purpose of their non-invasive identification by SERS techniques. The current standard procedure for dye analysis is a destructive procedure that is based on the removal of a sample from the work of art and its treatment with an appropriate reagent capable of dissolving the dye-aluminum complex and removing the dye from the textile fiber or other support. This reagent can be an acidic solution (e.g. the Wouters reference identified above, or the same H2O/EDTA/DMF mixture identified herein, with the difference that the procedure of the Tiedemann, E. J., and Yang, Y reference is carried out at boiling).

Solvent gels have been previously used in the art conservation field, as a means to selectively clean areas of paintings (in this sense, they are a refined version of commercially available gel paint strippers). The present invention, however, is the first method ever proven effective for the non-invasive analysis of insoluble dues contained in textiles, paintings, documents, and other items.

In view of the foregoing discussion, it is intended that the appended claims be interpreted as including the embodiments described herein, the alternatives mentioned above, and all equivalents thereto.

What is claimed is:

1. A process of identifying an organic dye in a work, comprising the steps of:
    applying a bead of a polymer gel to a portion of a work;
    removing the bead from the work;
    applying a SERS substrate to the bead; and
    examining the bead in accordance with a surface enhanced Raman scattering technique.

2. The process of claim 1, wherein the polymer gel is selected from the group consisting of 2-hydroxyethyl methacrylate; 2,3-dihydroxypropyl methacrylate; a 1:1 random copolymer of 2,3 dihydroxypropyl methacrylate with 2-hydroxyethyl methacrylate; and a cross-linked hydroxyalkyl methacrylate.

3. The process of claim 1, further comprising loading the bead with a solution containing at least water and a chelating agent.

4. The process of claim 3, wherein the chelating agent is selected from the group consisting of ethylene diamine tetraacetic acid and a sodium salt of ethylene diamine tetraacetic.

5. The process of claim 1, further comprising loading the bead with a solution containing at least an organic solvent and a chelating agent.

6. The process of claim 5, wherein the organic solvent is selected from the group consisting of dimethyl formammide, dimethyl sulfoxide and pyridine.

7. The process of claim 5, wherein an amount of the chelating agent is selected to be in a range extending substantially between 0.1% (weight/volume) to a percentage value at saturation.

8. The process of claim 1, further comprising loading the bead with a solution containing water, an organic solvent and a chelating agent.

9. The process of claim 8, wherein a ratio of the water to the organic solvent is selected to be an intermediate value between 1:10 water/organic solvent and 10:1 water/organic solvent.

10. The process of claim 1, wherein the SERS substrate is a silver, gold or copper colloid.

11. The process of claim 1, wherein the SERS substrate is comprised of silver, gold or copper nanoislands.

12. The process of claim 11, further comprising producing the silver, gold or copper nanoislands by evaporation under high vacuum.

13. The process of claim 1, further comprising the step of forming the polymer gel on an end of a sensing device.

14. The process of claim 13, wherein the sensing device is an optical fiber.

15. The process of claim 13, wherein the sensing device is a glass plate pre-coated with silver, gold, or copper nanoislands.

16. The process of claim 1, wherein the bead is applied to the work for a period of substantially between 10 minutes and eight hours.

17. The process of claim 1, wherein the step of removing the bead from the work is carried out without removing a sample from the work.

18. The process of claim 1, wherein the step of examining the bead includes identifying an organic dye in the work.

19. The process of claim 18, wherein the organic dye is an insoluble dye.

* * * * *